United States Patent

Farrar et al.

[11] Patent Number: 5,904,720
[45] Date of Patent: May 18, 1999

[54] HIP JOINT PROSTHESIS

[75] Inventors: Richard Farrar, Lymington, United Kingdom; Mary Elizabeth Schmidt, Pomfret Center, Conn.

[73] Assignee: Johnson & Johnson Professional, Inc., Raynham, Mass.

[21] Appl. No.: 08/909,619

[22] Filed: Aug. 12, 1997

[30] Foreign Application Priority Data

Nov. 12, 1996 [GB] United Kingdom .................... 9623540

[51] Int. Cl.$^6$ ........................................................ A61F 2/36
[52] U.S. Cl. ................................ 623/22; 623/18; 623/20; 623/19
[58] Field of Search ................................ 623/16, 18, 19, 623/20, 22, 23, 66

[56] References Cited

U.S. PATENT DOCUMENTS

| | | | |
|---|---|---|---|
| 3,744,061 | 7/1973 | Frost ........................................... | 623/22 |
| 3,865,585 | 2/1975 | Rademacher ............................... | 623/66 |
| 4,631,082 | 12/1986 | Andrews et al. .......................... | 75/235 |
| 4,714,468 | 12/1987 | Wang et al. ............................... | 623/16 |
| 4,718,908 | 1/1988 | Wigginton et al. ........................ | 623/23 |
| 4,904,267 | 2/1990 | Bruce et al. ............................... | 623/18 |
| 5,549,699 | 8/1996 | MacMahon et al. ....................... | 623/18 |
| 5,571,193 | 11/1996 | Kampner .................................... | 623/18 |

FOREIGN PATENT DOCUMENTS

| | | |
|---|---|---|
| 1126961 | 9/1968 | United Kingdom . |
| 9716138 | 5/1997 | WIPO ............................... A61F 2/30 |
| WO 9738650 | 10/1997 | WIPO ............................... A61F 2/32 |

OTHER PUBLICATIONS

R. Varano, J.D. Bobyn, and S. Yue. 1997. Characterization of Co–Cr–Mo Alloys Used in Hip Implant Articulating Surfaces, Materials Research Society Symposium Proceedings. 441:481–486.

Steicher, RM et al. "Investigation of the Tribological Behaviour of Metal–on–metal Combinations for Artificial Hip Joints," *Biomedizinische Technik*, vol. 35 No. 5/1990, pp. 3–7.

Protek AG, "Metasul, 'Metal–on–Metal Articulation'" Edition Feb. 1994, pp. 1–8.

Metasul®, Technical Information, Copyright 1993 by Allo Pro Ag, Lit. No. 1912e—Ed. Apr. 1994, 16 pp.

Semlitsch, M., et al., Long–Term Results with Metal/Metal Pairing in Artificial Joints, pp. 62–67. (Publication date unknown.)

R. M. Streicher et al., "Metal–on–metal articulation for artificial hip joints: laboratory study and clinical results,"210 Proc. Instn. Mech. Engrs. 223–232 (1996).

M. Schmidt et al., "Cobalt Chromium Molybdenum Metal Combination for Modular Hip Prostheses,"3295 Clinical Orthopaedics and Related Research 536–547 (1996).

*Primary Examiner*—Michael J. Milano
*Assistant Examiner*—Tram A. Nguyen
*Attorney, Agent, or Firm*—Nutter, McClennen & Fish, LLP

[57] ABSTRACT

A joint prosthesis having two mutually articulating components that are made of a metal alloy. One of the components is made of an alloy having a low carbon content (0.03 to 0.10 wt. %) and the other component is made of an alloy having a high carbon content (0.18 to 0.35 wt. %). The articulating components may be, for example, a hip head prosthesis and an acetabular cup prosthesis.

11 Claims, 3 Drawing Sheets

HIP JOINT PROSTHESIS

CROSS REFERENCE TO RELATED APPLICATIONS

This application is based on and claims priority from United Kingdom Patent Application No. 9623540.3, filed Nov. 12, 1996.

STATEMENT REGARDING FEDERALLY SPONSORED RESEARCH

Not applicable.

FIELD OF THE INVENTION

This invention relates to artificial joints, such as hip joint prostheses, comprising two or more components with closely conforming articulating surfaces. More particularly, the invention relates to such artificial joints wherein the articulating surfaces are made of metal.

Artificial joints, such as hip joints, shoulder joints and knee joints, are extremely widely used in orthopaedic surgery. Hip joint prostheses are particularly common. Such prostheses comprise an acetabular component, often referred to as an acetabular cup, and a femoral component. The acetabular component is usually of generally hemispherical shape, and it provides a generally hemispherical inner articulation surface. The femoral component generally comprises a spherical or near-spherical head, attached to an elongate stem. In use, the elongate stem is located in the intramedullary canal of the femur, and the head is located within the acetabular component, to provide articulation between the femur and the acetabulum. In the first hip joint prostheses, both the inner articulation surface of the acetabular component and the head portion of the femoral component were made of metal, such as cast cobalt chromium alloy. However, such metal-on-metal prostheses were largely superseded by the use of a modified form of acetabular cup, comprising a metal outer shell, and an ultrahigh molecular weight polyethylene insert. Although prostheses of the latter type have been used in very large numbers, there is some concern that articulation of a metal head in a polyethylene cup causes significant erosion of the cup, with polyethylene debris being released into the surrounding tissue. For this reason, attention is again being focused on metal-on-metal hip joint prostheses.

One currently available metal-on-metal prosthesis is the Metasul™ product distributed by Protek AG. The product literature for this prosthesis specifies that the cup and the femoral component are both made from a forged CoCrMo alloy called Protasul®-21WF. Protasul®-21WF is believed to have a typical carbon content of 0.2%.

SUMMARY OF THE INVENTION

Surprisingly, we have found that improved wear is obtained if the two articulating surfaces of a metal-on-metal joint prosthesis are formed from metals which are mismatched with respect to their carbon content. Accordingly, the present invention provides a joint prosthesis comprising a first component and a second component, the articulation surfaces of the first component and the second component both being formed from a cobalt chromium alloy, characterized in that the articulation surface of the first component or the second component is formed from a cobalt chromium alloy having less than 0.1% carbon by weight, and the other articulation surface is formed from a cobalt chromium alloy comprising at least 0.18% carbon by weight.

Alloys having less than 0.1 wt. % carbon are hereafter referred to as low carbon content alloys. Preferably, low carbon content alloys used in the prostheses of the present invention contain about 0.03 to 0.10 wt. % carbon, and most preferably about 0.06 to 0.07 wt. % carbon.

Alloys containing at least 0.18 wt. % carbon are hereafter referred to as high carbon content alloys. Preferably, high carbon content alloys used in the prostheses of the present invention contain from 0.20 to 0.35 wt. % carbon, and most preferably about 0.22 wt. % carbon. The alloys which are used to form the prostheses of the present invention preferably comprise from 58 to 69% cobalt, from 26 to 30% chromium, from 5 to 7% molybdenum and no more than 5% of other elements, all percentages being by weight. More preferably, such alloys comprise no more than 1 wt. % nickel, 0.75 wt. % iron, 1 wt. % silicon, 1 wt. % manganese and 0.25 wt. % nitrogen. Although wrought alloys are preferred, cast or forged alloys may also be used. Wrought alloys having the composition set out above are described in ASTM F1537, while forged alloys of the same composition are described in ASTM F799. The composition of cast alloys differs from that of wrought and forged alloys in that chromium is present in cast alloys at 27–30% by weight. A suitable cast alloy is ASTM F75.

Preferably, the joint prosthesis is a hip joint prosthesis wherein the first component is an acetabular cup and the second component is a femoral component.

The articulating surfaces of prostheses according to the invention will usually be substantially congruent. In the case of hip joint prostheses, such surfaces will be generally spherical, preferably with a departure from roundness no greater than about 10 $\mu$m when measured in accordance with the minimum zone center method given in ISO 4291. More preferably, the articulating surfaces will have roundness errors no greater than 8 $\mu$m, and most preferably no greater than 5 $\mu$m.

In order to minimize wear, the articulating surfaces of the prostheses of the invention will usually also be highly polished. Preferably, the articulating surfaces will have an $R_a$ value (average roughness; as measured in accordance with ISO 468) no greater than 0.1 $\mu$m, and more preferably no greater than 0.05 $\mu$m. Particularly preferred prostheses according to the invention will have articulating surfaces with an $R_a$ value no greater than 0.02 $\mu$m.

Hip joint prostheses according to the present invention may take any of various forms. For example, the femoral component may be of the cemented or cementless type, and it may be provided with a collar for transmission of load to the calcar of the femur. Similarly, the acetabular component may be of the cemented or cementless type.

When cementless femoral or acetabular components are used in accordance with the present invention, they may be provided with porous outer surfaces to encourage attachment of bone, as is well known in the art. Suitable porous surfaces may be provided by a variety of procedures such as simple rough blasting, chemical etching or application of plasma sprayed layers. Sintered porous coating comprising beads, mesh or fibre pads may also be used.

Cemented prostheses in accordance with the present invention will generally have relatively smooth surface finishes to prevent abrasion of the cement.

It will be understood that the prostheses of the present invention need not be made entirely from cobalt chrome alloy. For example, an acetabular cup may comprise a cobalt chrome alloy insert which provides the articulating surface, and an outer shell formed from titanium, titanium alloy, cobalt chrome alloy or even ceramic. Stainless steel could also be used for the outer shell if the insert and the shell are electrically insulated to prevent galvanic corrosion.

BRIEF DESCRIPTION OF THE DRAWINGS

Similarly, a femoral prosthesis may comprise a cobalt chrome alloy head, and a stem formed from titanium, titanium alloy or cobalt chrome alloy.

An embodiment of a joint prosthesis in accordance with the present invention in the form of a hip joint prosthesis is now described with reference to the accompanying drawings, in which.

DETAILED DESCRIPTION OF THE INVENTION

Figure 1:
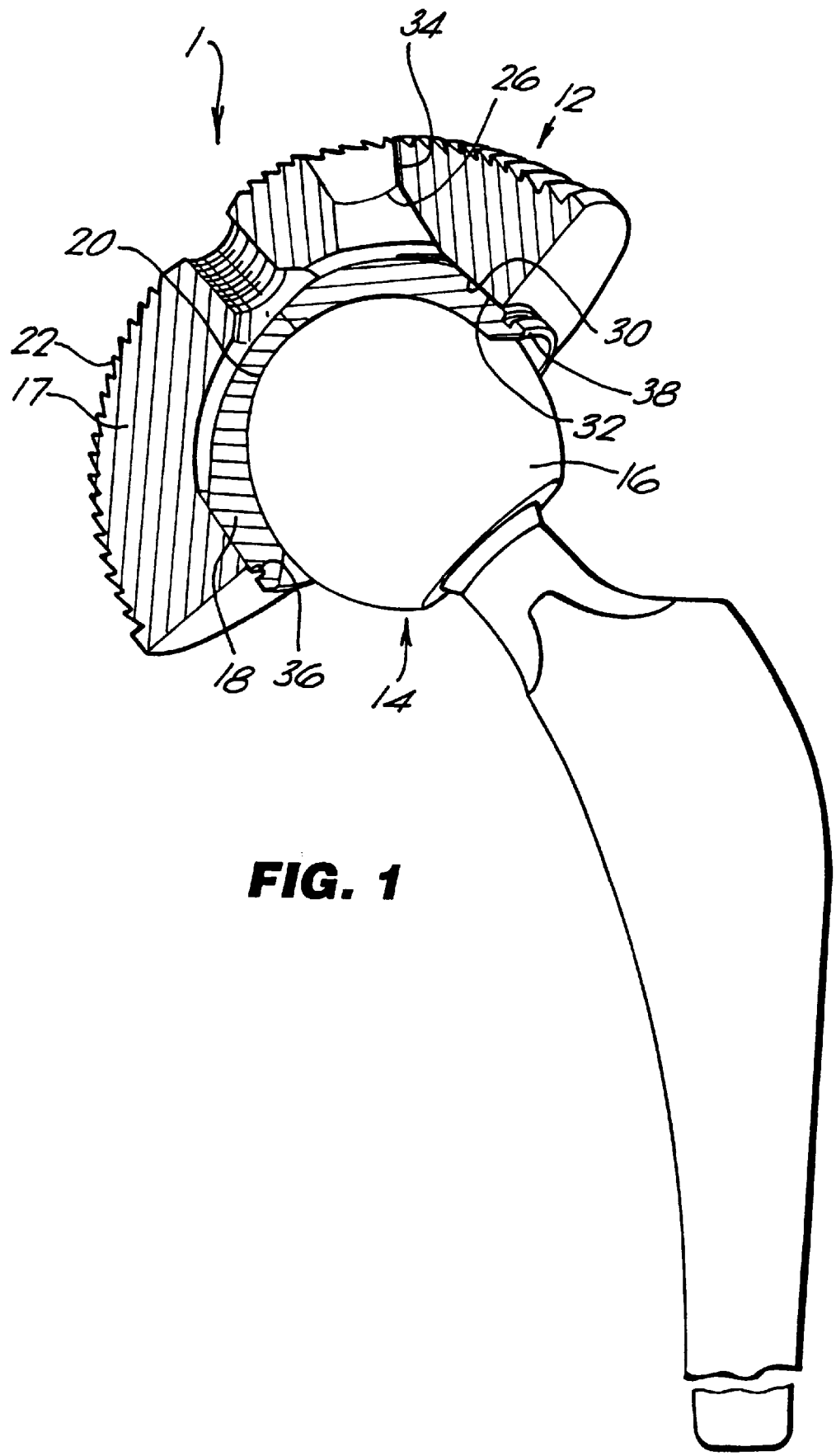
FIG. 1 is a cross-sectional view of an acetabular component and a femoral head of the hip joint prosthesis.
Figure 2:
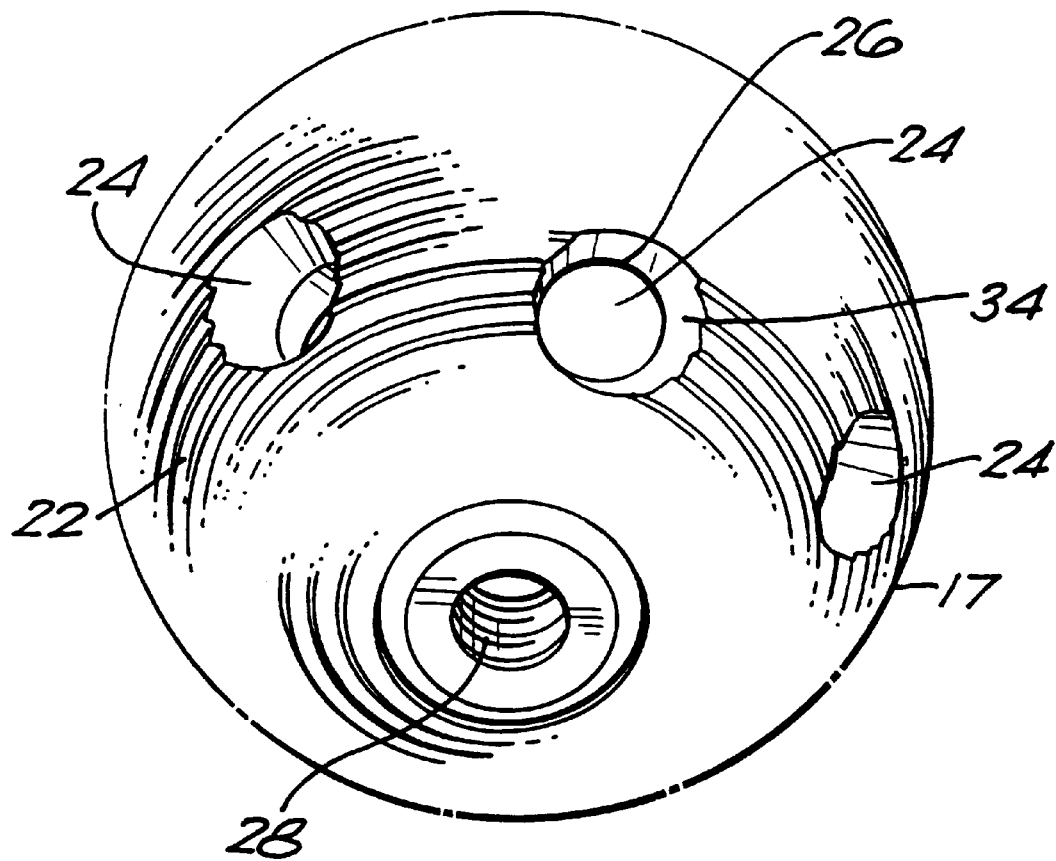
FIG. 2 is a perspective view of the outer shell of the acetabular component of FIG. 1.
Figure 3:
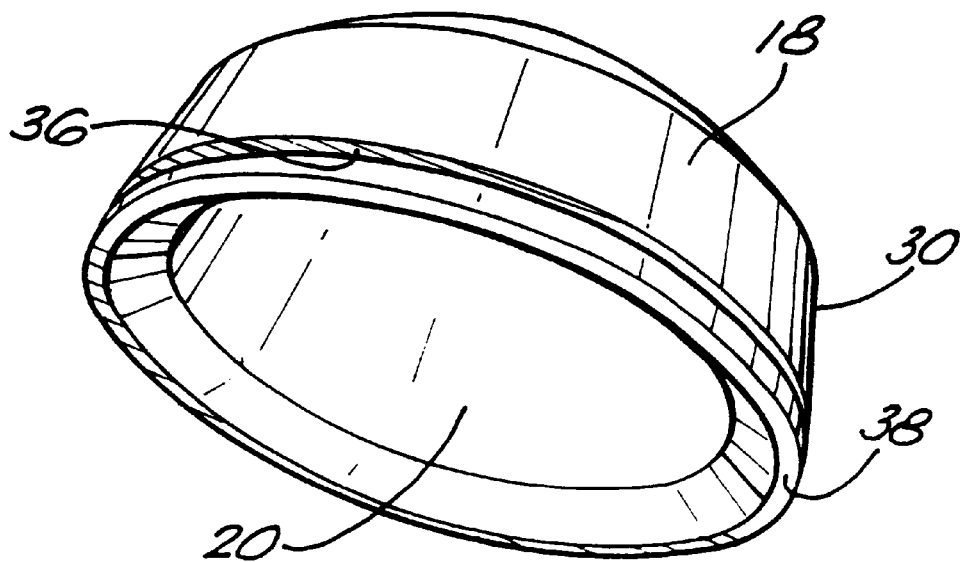
FIG. 3 is a perspective view of an insert of the acetabular component of FIG. 1.

FIG. 1 shows a hip prosthesis 1 comprising an acetabular component 12 and a femoral component 14. The acetabular component 12 is formed of an insert 18 with an inner articulating surface 20, the insert 18 being disposed within a shell 17. The insert 18 preferably is made of a high carbon content wrought cobalt chrome alloy conforming to ASTM F1537 and having a carbon content in the range of approximately 0.20 to 0.35 wt. %, and most preferably about 0.22 wt. %, while the shell 17 is of a titanium alloy (Ti6A14V).

The inner articulating surface 20 of the insert 18 is substantially congruent with the surface of a femoral head 16 of a femoral component 14. The femoral component 14 also comprises a femoral stem to which the femoral head 16 is attachable. Both the head 16 and the stem preferably are of a cobalt chrome alloy conforming to ASTM F1537. However, in contrast to the insert 18, the alloy from which the head 16 is formed is a low carbon content cobalt chrome alloy with a carbon content in the range of approximately 0.03 to 0.10 wt. %, and most preferably about 0.06 to 0.07 wt. %.

The insert 18 is generally hemispherical and has a portion of its outer surface 30 in the form of a band adjacent the rim 38 of the insert 18 which is angled to form a taper fit with an angled inner surface 32 of the shell 17. There is an area of clearance between the remainder of the outer surface of the insert 18 and the inner surface of the shell 17. The insert 18 has a groove 36 at its rim 38 in which an extraction instrument can be located.

The shell 17 of the acetabular component 12 has a ridged outer surface 22 which can be coated as discussed above to enhance the attachment of bone. The shell 17 of the described embodiment has three apertures 24 through which screws are placed for securement of the shell 17 to the patient's hip bone. The screws normally are attached prior to the insertion of the insert 18 into the shell 17. The apertures 24 are unthreaded and are dual tapered 34 outwardly towards the inner and outer surfaces of the shell 17. The smallest diameter 26 of each aperture 24 prevents the screw from passing through the aperture 24. The shell 17 also has an apical threaded aperture 28 for instrumentation attachment and for viewing.

Experimental

The wear of hip joint prosthesis components was assessed by subjecting an acetabular component and a femoral component to repeated articulation representative of a normal walking cycle. Testing was conducted using a model EW-12 hip simulator, manufactured by Materials Technology Inc., La Canada, Calif.

The femoral heads used in this evaluation had a diameter of 28 mm. The nominal clearance (cup diameter minus head diameter) between the femoral heads and the acetabular cups during testing was 0.050 mm. Actual clearances ranged from 0.045 mm to 0.054 mm. The components were subjected to a loading curve during testing that is equivalent to that developed during a walking cycle. Peak load was approximately 2000N.

During testing the hip prostheses were completely immersed in bovine serum. Tests were conducted for up to two million cycles. Wear was assessed by measuring the total weight loss of the two components during testing.

In all cases, the prostheses had articulation surfaces formed from cobalt chromium alloy conforming to ASTM F1537. However, the samples differed in the carbon content of the alloy used. Low-carbon (approximately 0.06 wt. % carbon) femoral components were matched with either low-carbon or high-carbon (approximately 0.22 wt. % carbon) acetabular cups, and high-carbon femoral components were similarly matched with either low-carbon or high-carbon cups. Surprisingly, the highest average wear (weight loss) was observed for prostheses in which the femoral head and the acetabular cup were both formed from low carbon content alloy, or both from high carbon content alloy. The lowest average wear (weight loss) was observed for prostheses in which a low carbon content alloy was used for the femoral head and a high carbon content alloy was used for the acetabular cup (or vice versa).

Figure 4:
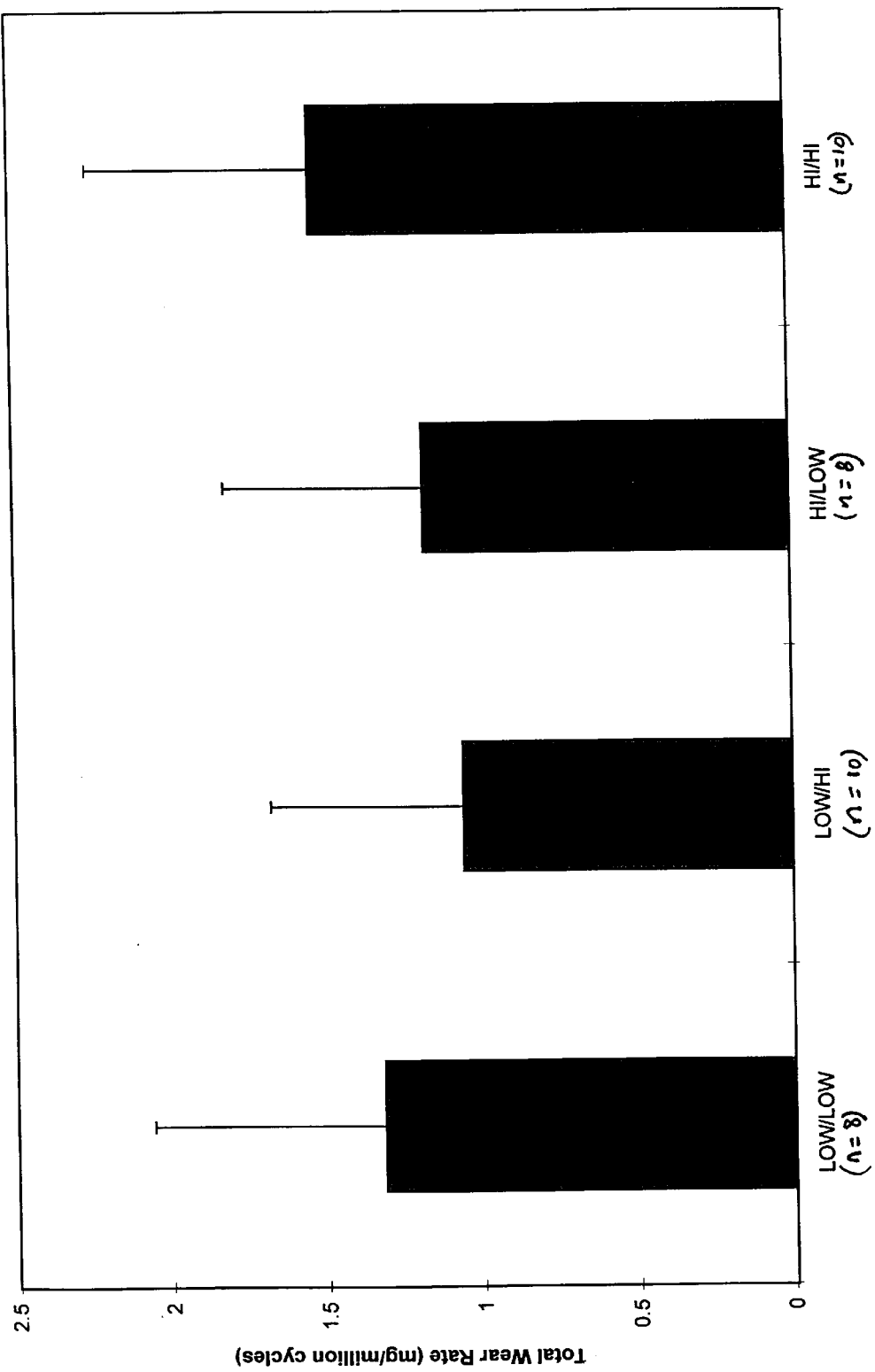
FIG. 4 is a chart illustrating the data combined for all tests.

The data combined for all tests are illustrated in the chart shown in FIG. 4.

What is claimed is:

1. A joint prosthesis comprising a first component and a second component, each of the first component and the second component having an articulation surface formed from a cobalt chromium alloy, wherein the articulation surface of the first component contacts the articulation surface of the second component, characterized in that the articulation surface of one of either the first component or the second component is formed from a cobalt chromium alloy having less than 0.10% carbon by weight, and the articulation surface of the other of either the first component and the second component is formed from a cobalt chromium alloy comprising at least 0.18% carbon by weight.

2. A prosthesis according to claim 1 wherein the articulation surface of one of either the first component or the second component is formed from a cobalt chromium alloy comprising from 0.03 to 0.07% carbon by weight, and the articulation surface of the other of either the first component and the second component is formed from a cobalt chromium alloy comprising 0.20 to 0.35% carbon by weight.

3. A prosthesis according to claim 1 wherein the first component and the second component are formed from an alloy comprising from 58 to 69 wt. % cobalt, from 26 to 30 wt. % chromium, from 5 to 7 wt. % molybdenum and no more than 5 wt. % (in total) of other elements.

4. A prosthesis according to claim 3 wherein said alloy comprises no more than 1 wt. % nickel, 0.75 wt. % iron, 1 wt. % silicon, 1 wt. % manganese and 0.25 wt. % nitrogen.

5. A prosthesis according to claim 4 wherein said alloy is wrought alloy.

6. A prosthesis according to claim 5 wherein said wrought alloy conforms to ASTM F1537.

7. A prosthesis according to claim 1 wherein the prosthesis is a hip joint prosthesis.

8. A prosthesis according to claim 7 wherein the first component is a hip head prosthesis and the second component is an acetabular cup prosthesis.

9. A hip joint prosthesis, comprising an acetabular cup having an articulation surface; and a femoral head having an articulation surface which contacts the articulation surface of the acetabular cup, wherein the articulation surface of one of the acetabular cup and the femoral head is made of a metal alloy having a low carbon content and the articulation surface of the other of the acetabular cup and the femoral head is made of a metal alloy having a high carbon content.

10. A hip joint prosthesis according to claim 9 wherein the carbon content of the low carbon content metal alloy is in the range of about 0.03 to 0.10 wt. % carbon.

11. A hip joint prosthesis according to claim 9 wherein the carbon content of the high carbon content metal alloy is in the range of about 0.18 to 0.35 wt. % carbon.

* * * * *